US012795181B2

(12) United States Patent
Peine et al.

(10) Patent No.: US 12,795,181 B2

(45) Date of Patent: Nov. 10, 2026

(54) SURGICAL ROBOTIC SYSTEM AND METHOD WITH MULTIPLE CAMERAS

(71) Applicant: Covidien LP, Mansfield, MA (US)

(72) Inventors: William J. Peine, Ashland, MA (US); Jared N. Farlow, Los Angeles, CA (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 108 days.

(21) Appl. No.: 18/461,630

(22) Filed: Sep. 6, 2023

(65) Prior Publication Data

US 2024/0137583 A1 Apr. 25, 2024
US 2024/0236384 A9 Jul. 11, 2024

Related U.S. Application Data

(60) Provisional application No. 63/418,854, filed on Oct. 24, 2022.

(51) Int. Cl.
*A61B 1/05* (2006.01)
*A61B 34/00* (2016.01)
(Continued)

(52) U.S. Cl.
CPC ........... *H04N 21/234* (2013.01); *A61B 34/20* (2016.02); *A61B 34/25* (2016.02); *A61B 34/30* (2016.02);
(Continued)

(58) Field of Classification Search
CPC .. H04N 21/234; H04N 13/117; H04N 13/156; H04N 13/271; H04N 13/239; A61B 34/20; A61B 34/25; A61B 34/30; A61B 34/71; A61B 2034/105; A61B 2034/107; A61B 2034/2057; A61B 2090/365;
(Continued)

(56) References Cited

U.S. PATENT DOCUMENTS 6,132,368 A 10/2000 Cooper
6,206,903 B1 3/2001 Ramans
(Continued)

FOREIGN PATENT DOCUMENTS

WO WO-2022103770 A1 * 5/2022 ......... A61B 1/00009

OTHER PUBLICATIONS

Extended European Search Report issued in corresponding application EP 23205339.7 dated Mar. 15, 2024 (8 pages).

*Primary Examiner* — Patrick E Demosky
(74) *Attorney, Agent, or Firm* — Carter, DeLuca & Farrell, LLP

(57) ABSTRACT

An imaging system includes a first camera configured to capture a first video stream of a first tissue surface and a second camera configured to capture a second video stream of a second tissue surface, the first tissue surface opposing the second tissue surface of the tissue. The system also includes a video processing device configured to receive the first video stream from the first camera and the second video stream from the second camera and modify at least one the first video stream or the second video stream based on one the first video stream or the second video stream to generate a 3D volume having a modified video stream. The system further includes a first screen coupled to the video processing device and configured to display the 3D volume with the modified video stream.

20 Claims, 9 Drawing Sheets

(51) Int. Cl.

| | |
|---|---|
| ***A61B 34/20*** | (2016.01) |
| ***A61B 34/30*** | (2016.01) |
| ***G06T 7/50*** | (2017.01) |
| ***H04N 13/117*** | (2018.01) |
| ***H04N 13/156*** | (2018.01) |
| ***H04N 13/239*** | (2018.01) |
| ***H04N 13/271*** | (2018.01) |
| ***H04N 21/234*** | (2011.01) |
| *A61B 34/10* | (2016.01) |
| *A61B 90/00* | (2016.01) |

(52) U.S. Cl.

CPC ................ *A61B 34/71* (2016.02); *G06T 7/50* (2017.01); *H04N 13/117* (2018.05); *H04N 13/156* (2018.05); *H04N 13/239* (2018.05); *H04N 13/271* (2018.05); *A61B 2034/105* (2016.02); *A61B 2034/107* (2016.02); *A61B 2034/2057* (2016.02); *A61B 2090/365* (2016.02); *A61B 2090/367* (2016.02); *A61B 2090/371* (2016.02); *G06T 2200/04* (2013.01); *G06T 2207/10016* (2013.01); *G06T 2207/10028* (2013.01); *G06T 2207/20221* (2013.01); *G06T 2207/30204* (2013.01)

(58) Field of Classification Search

CPC ........ A61B 2090/367; A61B 2090/371; G06T 7/50; G06T 2200/04; G06T 2207/10016; G06T 2207/10028; G06T 2207/20221; G06T 2207/30204

See application file for complete search history.

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |

(56) References Cited

U.S. PATENT DOCUMENTS 8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,043,027 B2 5/2015 Durant et al.
9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,165 B2 10/2018 Power
10,092,344 B2 10/2018 Mohr et al.
10,123,844 B2 11/2018 Nowlin
10,188,471 B2 1/2019 Brisson
10,201,390 B2 2/2019 Swarup et al.
10,213,202 B2 2/2019 Flanagan et al.
10,258,416 B2 4/2019 Mintz et al.

(56) References Cited

U.S. PATENT DOCUMENTS 10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs, II et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.
11,109,925 B2 9/2021 Cooper et al.
11,116,578 B2 9/2021 Hoffman et al.
11,129,683 B2 9/2021 Steger et al.
11,135,029 B2 10/2021 Suresh et al.
11,147,552 B2 10/2021 Burbank et al.
11,147,640 B2 10/2021 Jarc et al.
11,154,373 B2 10/2021 Abbott et al.
11,154,374 B2 10/2021 Hanuschik et al.
11,160,622 B2 11/2021 Goldberg et al.
11,160,625 B2 11/2021 Wixey et al.
11,161,243 B2 11/2021 Rabindran et al.
11,166,758 B2 11/2021 Mohr et al.
11,166,770 B2 11/2021 DiMaio et al.
11,166,773 B2 11/2021 Ragosta et al.
11,173,597 B2 11/2021 Rabindran et al.
11,185,378 B2 11/2021 Weir et al.
11,191,596 B2 12/2021 Thompson et al.
11,197,729 B2 12/2021 Thompson et al.
11,213,360 B2 1/2022 Hourtash et al.
11,221,863 B2 1/2022 Azizian et al.
11,234,700 B2 2/2022 Ragosta et al.
11,241,274 B2 2/2022 Vaders et al.
11,241,290 B2 2/2022 Waterbury et al.
11,259,870 B2 3/2022 DiMaio et al.
11,259,884 B2 3/2022 Burbank
11,272,993 B2 3/2022 Gomez et al.
11,272,994 B2 3/2022 Saraliev et al.
11,291,442 B2 4/2022 Wixey et al.
11,291,513 B2 4/2022 Manzo et al.
11,376,002 B2 7/2022 Shelton, IV et al.
11,376,098 B2 7/2022 Shelton, IV et al.
11,381,759 B2 7/2022 Zhao et al.
11,382,621 B2 7/2022 Scheib et al.
11,382,624 B2 7/2022 Harris et al.
11,382,625 B2 7/2022 Huitema et al.
11,382,626 B2 7/2022 Shelton, IV et al.
11,382,627 B2 7/2022 Huitema et al.
11,382,638 B2 7/2022 Harris et al.
11,382,644 B2 7/2022 Schoettgen et al.
11,389,160 B2 7/2022 Shelton, IV et al.
11,389,255 B2 7/2022 DiMaio et al.
11,399,906 B2 8/2022 Shelton, IV et al.
11,406,379 B2 8/2022 Hess et al.
11,410,259 B2 8/2022 Harris et al.
11,419,630 B2 8/2022 Yates et al.
11,424,027 B2 8/2022 Shelton, IV
11,432,888 B2 9/2022 Diolaiti et al.
11,432,893 B2 9/2022 Itkowitz et al.
11,432,895 B2 9/2022 Loh et al.
11,439,390 B2 9/2022 Patel et al.
11,439,391 B2 9/2022 Bruns et al.
11,468,791 B2 10/2022 Jarc et al.
11,471,155 B2 10/2022 Shelton, IV et al.
11,471,221 B2 10/2022 Zhao et al.
11,478,308 B2 10/2022 Hoffman et al.
11,490,977 B2 11/2022 Schena et al.
11,497,499 B2 11/2022 Shelton, IV et al.
11,504,119 B2 11/2022 Shelton, IV et al.
11,504,124 B2 11/2022 Patel et al.
11,510,743 B2 11/2022 Shelton, IV et al.
11,517,312 B2 12/2022 Wixey
11,517,325 B2 12/2022 Shelton, IV et al.
11,518,048 B2 12/2022 Saraliev et al.
2012/0053402 A1 3/2012 Conlon et al.
2014/0179997 A1 6/2014 von Grünberg
2017/0085855 A1* 3/2017 Roberts ................ H04N 13/257
2019/0183591 A1* 6/2019 Johnson ................. B25J 9/1666
2020/0000530 A1 1/2020 DeFonzo et al.
2020/0100855 A1 4/2020 Leparmentier et al.
2020/0107886 A1* 4/2020 Govari ................... A61B 5/062
2020/0261155 A1 8/2020 Popovic et al.
2021/0085164 A1* 3/2021 Schelter ............. A61B 1/00009
2023/0110791 A1* 4/2023 Shelton, IV ........... A61B 90/36
606/130
2024/0016539 A1* 1/2024 Kellnberger ........... A61B 18/14
2025/0134488 A1* 5/2025 Kaouk ..................... A61B 8/12

* cited by examiner

SURGICAL ROBOTIC SYSTEM AND METHOD WITH MULTIPLE CAMERAS

CROSS-REFERENCE TO RELATED APPLICATIONS

This application claims the benefit of the filing date of provisional U.S. Patent Application No. 63/418,854 filed on Oct. 24, 2022. The entire disclosure of the foregoing application is incorporated by reference herein.

BACKGROUND

Surgical robotic systems are currently being used in a variety of surgical procedures, including minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body. However, a single endoscopic camera provides a limited field of view of the surgical site. Thus, there is a need for a system that receives video from multiple cameras and provides an augmented view of the surgical site.

SUMMARY

According to one aspect of the above embodiment, an imaging system is disclosed which includes a first camera configured to capture a first video stream of a first tissue surface and a second camera configured to capture a second video stream of a second tissue surface, the first tissue surface opposing the second tissue surface of the tissue. The system also includes a video processing device configured to receive the first video stream from the first camera and the second video stream from the second camera and modify at least one the first video stream or the second video stream based on one the first video stream or the second video stream to generate a modified video stream. The system further includes a first screen coupled to the video processing device and configured to display the modified video stream.

Implementations of the above embodiment may include one or more of the following features. According to one aspect of the above embodiment, the imaging system may include a second screen coupled to the video processing device. The video processing device may be configured to output at least one of the first video stream, the second video stream, or the modified video stream on at least one of the first screen or the second screen. The video processing device may be further configured to generate a virtual marker, such as a shape, plane, boundary, line, etc. across in the modified video stream to demarcate a region of tissue. The virtual marker may be placed at a representation of a location of the second camera. In modifying the first video stream, the video processing device may be further configured to remove a portion of the first video stream. In modifying the first video stream, the video processing device may be also configured to fill in the portion of the first video stream with a reconstructed portion of the second video stream. The video processing device may be further configured to generate a depth map of the first and second tissue surfaces and generate the reconstructed portion based on the depth map.

According to another aspect of the above embodiment, a surgical robotic system is disclosed which includes first robotic arm including a first camera located at a first position and configured to capture a first video stream of a first tissue surface. The system also includes a second robotic arm including a second camera located at a second position and configured to capture a second video stream of a second tissue surface, the first tissue surface opposing the second tissue surface of the tissue and a third robotic arm including a surgical instrument. The system further includes a video processing device configured to receive the first video stream from the first camera and the second video stream from the second camera and combine the first video stream based on the second video stream to generate a combined video stream based on the first position and the second position. The video processing device is further configured to generate a 3D volume including a trajectory of at least one of the first camera, the second camera, or the instrument based on the combined video stream. The system further includes a surgeon console including a first screen coupled to the video processing device and configured to display the combined video stream.

Implementations of the above embodiment may include one or more of the following features. According to one aspect of the above embodiment, the surgeon console may further include a second screen coupled to the video processing device. The video processing device may be configured to output at least one of the first video stream, the second video stream, or the modified video stream on at least one of the first screen or the second screen. The video processing device may be further configured to generate a virtual marker in the modified video stream. The virtual marker may be placed at a location within a field of view of the second camera. In modifying the first video stream, the video processing device may be further configured to remove a portion of the first video stream. In modifying the first video stream, the video processing device may be also configured to fill in the portion of the first video stream with a reconstructed portion of the second video stream. The video processing device may be further configured to generate a depth map of the first and second tissue surfaces and generate the reconstructed portion based on the depth map.

According to a further aspect of the above embodiment, a method of imaging tissue is disclosed which includes capturing a first video stream of a first tissue surface at a first camera, and capturing a second video stream of a second tissue surface at a second camera, the first tissue surface opposing the second tissue surface of the tissue. The method also includes receiving the first video stream from the first camera at a video processing device and receiving the second video stream from the second camera at the video processing device. The method further includes modifying the first video stream based on the second video stream to generate a modified video stream. The method additionally includes displaying the modified video stream on a screen coupled to the video processing device.

Implementations of the above embodiment may include one or more of the following features. According to one aspect of the above embodiment, modifying the first video stream at the video processing device may further include removing a portion of the first video stream. Modifying the first video stream at the video processing device may also include filling in the portion of the first video stream with a reconstructed portion of the second video stream. Modifying the first video stream at the video processing device may additionally include generating a depth map of the first and second tissue surfaces and generate the reconstructed portion based on the depth map.

BRIEF DESCRIPTION OF THE DRAWINGS

Various embodiments of the present disclosure are described herein with reference to the drawings wherein.

DETAILED DESCRIPTION

Figure 1:
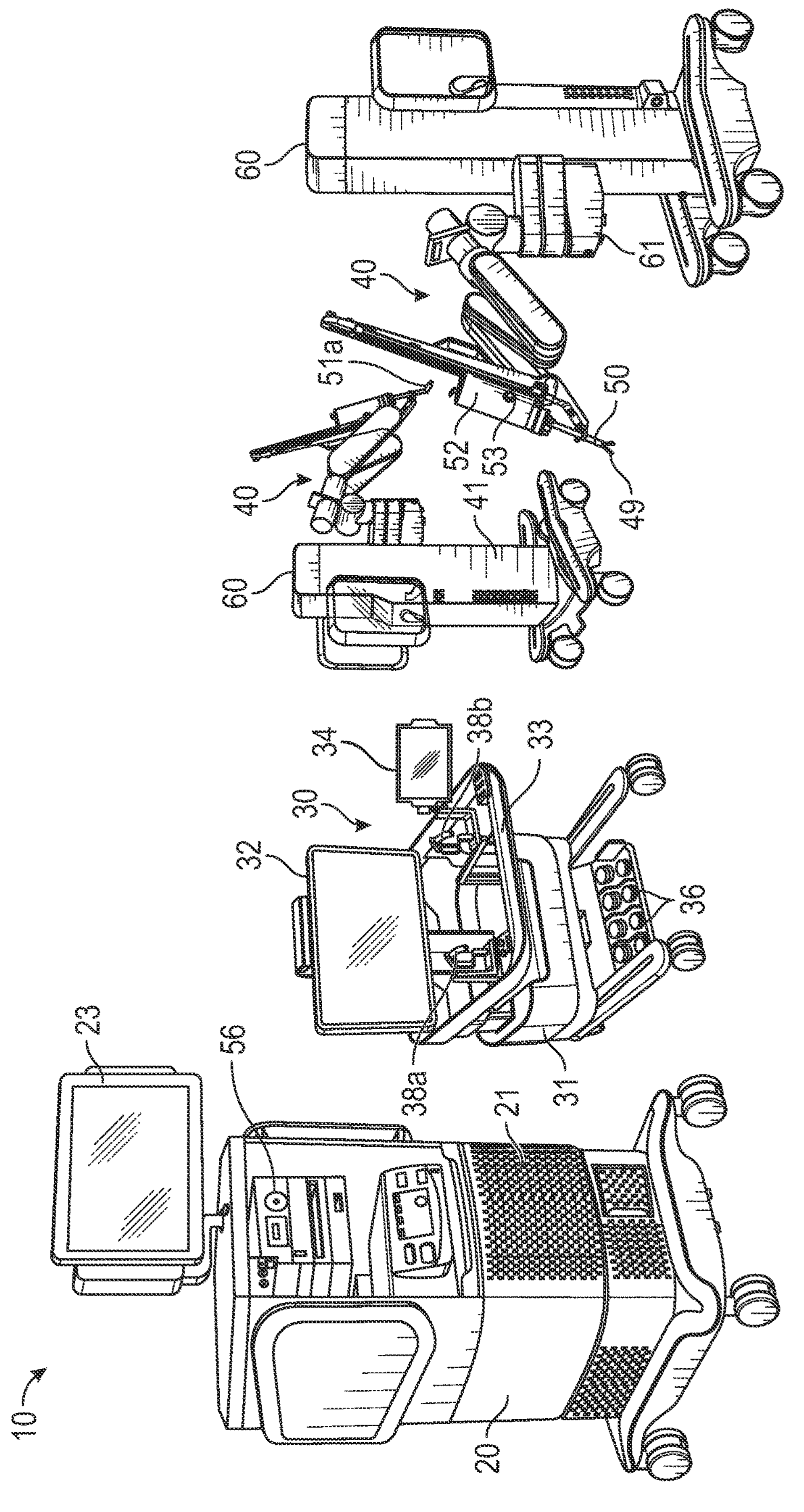
FIG. 1 is a schematic illustration of a surgical robotic system including a control tower, a console, and one or more surgical robotic arms each disposed on a movable cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices. The user input is processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement commands and to generate a torque commands for activating one or more actuators of the robotic arm, which would, in turn, move the robotic arm in response to the movement commands.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

The surgeon console 30 includes a first screen 32, which displays a video feed of the surgical site provided by camera **51*a* disposed on the robotic arm 40, and a second screen 34, which displays a user interface for controlling the surgical robotic system 10. The first screen 32 and second screen 34** may be touchscreens allowing for displaying various graphical user inputs.

The surgeon console 30 also includes a plurality of user interface devices, such as foot pedals 36 and a pair of hand controllers **38*a* and 38*b* which are used by a user to remotely control robotic arms 40. The surgeon console further includes an armrest 33 used to support clinician's arms while operating the hand controllers 38*a* and 38*b***.

The control tower 20 includes a screen 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the hand controllers **38*a* and 38*b*. The foot pedals 36 may be used to enable and lock the hand controllers 38*a* and 38*b*, repositioning camera movement and electrosurgical activation/deactivation. In particular, the foot pedals 36 may be used to perform a clutching action on the hand controllers 38*a* and 38*b*. Clutching is initiated by pressing one of the foot pedals 36, which disconnects (i.e., prevents movement inputs) the hand controllers 38*a* and/or 38*b* from the robotic arm 40 and corresponding instrument 50 or camera 51*a* attached thereto. This allows the user to reposition the hand controllers 38*a* and 38*b* without moving the robotic arm(s) 40 and the instrument 50 and/or camera 51*a***. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
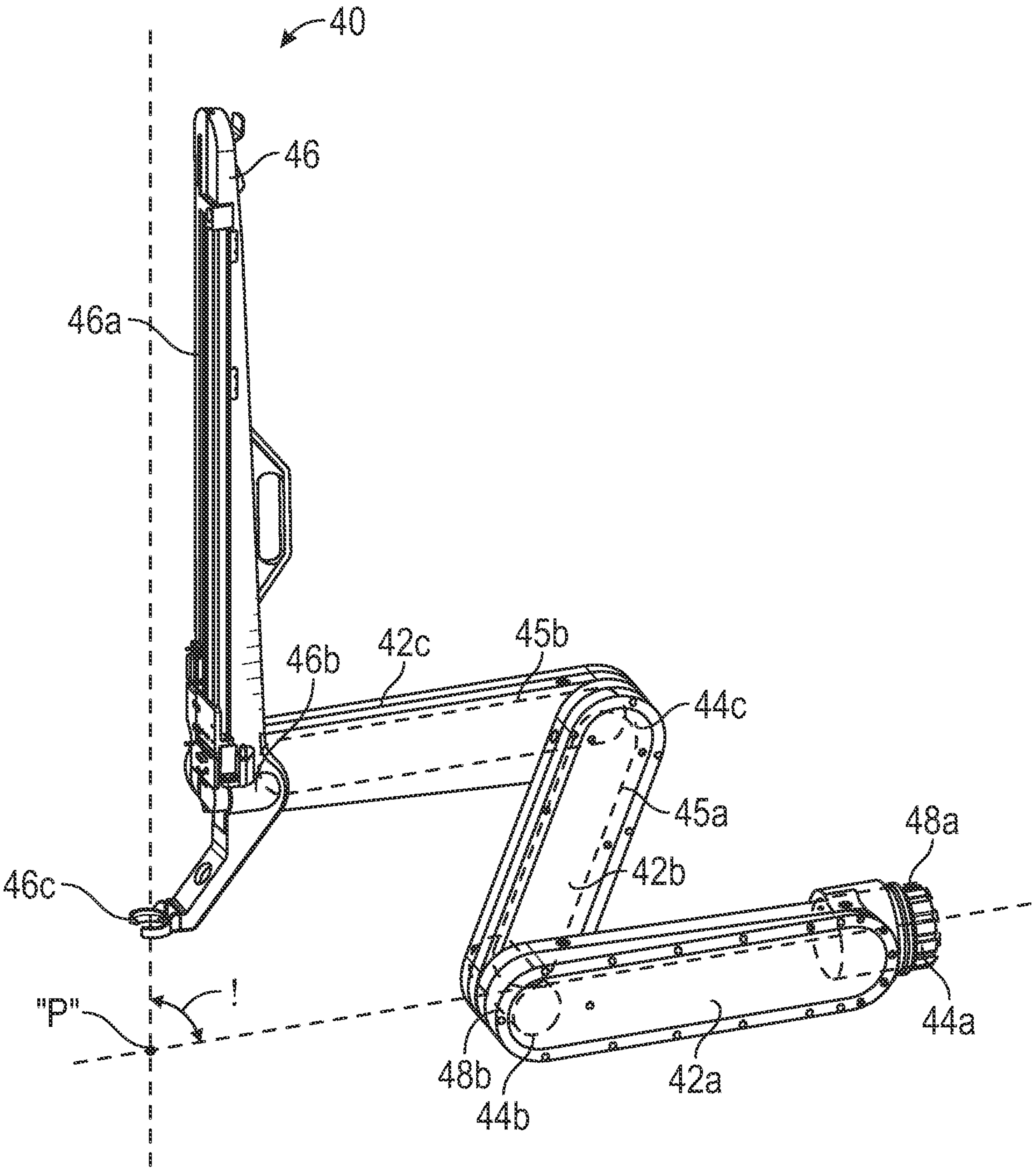
FIG. 2 is a perspective view of a surgical robotic arm of the surgical robotic system of FIG. 1 according to an embodiment of the present disclosure.
Figure 3:
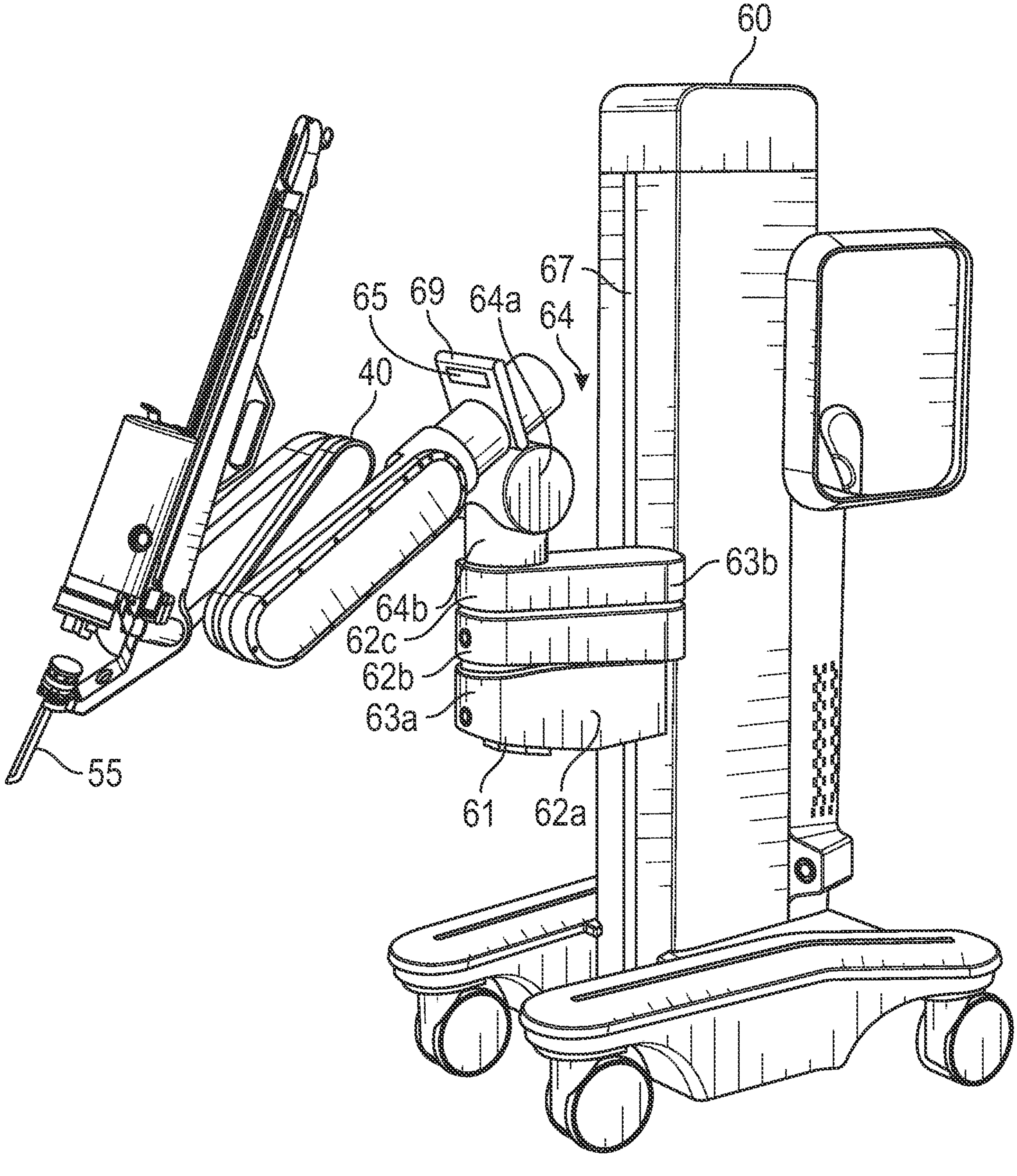
FIG. 3 is a perspective view of a movable cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the movable cart 60 and defines a first longitudinal axis. With reference to FIG. 3, the movable cart 60 includes a lift 67 and a setup arm 61, which provides a base for mounting of the robotic arm 40. The lift 67 allows for vertical movement of the setup arm 61. The movable cart 60 also includes a display 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle $\theta$ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle $\theta$. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51*a* and is configured to move (e.g., rotate) and actuate the instrument 50 and/or the camera 51*a*. IDU 52 transfers actuation forces from its actuators to the surgical instrument 50 to actuate components an end effector 49 of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
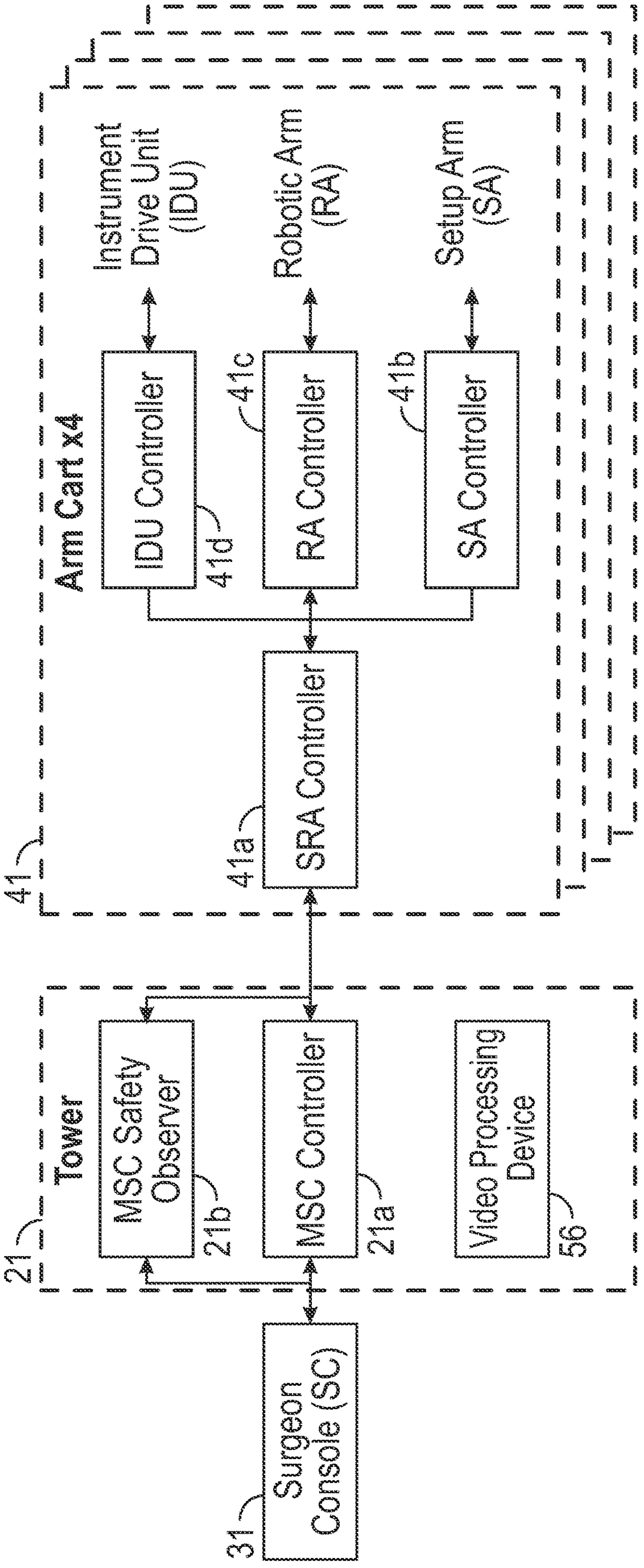
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the hand controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the hand controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the hand controller controlling the robotic arm 40, e.g., the hand controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the hand controllers 38*a* may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the hand controller 38*a* is then scaled by a scaling function executed by the controller 21*a*. In embodiments, the coordinate position may be scaled down and the orientation may be scaled up by the scaling function. In addition, the controller 21*a* may also execute a clutching function, which disengages the hand controller 38*a* from the robotic arm 40. In particular, the controller 21*a* stops transmitting movement commands from the hand controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the hand controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the hand controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
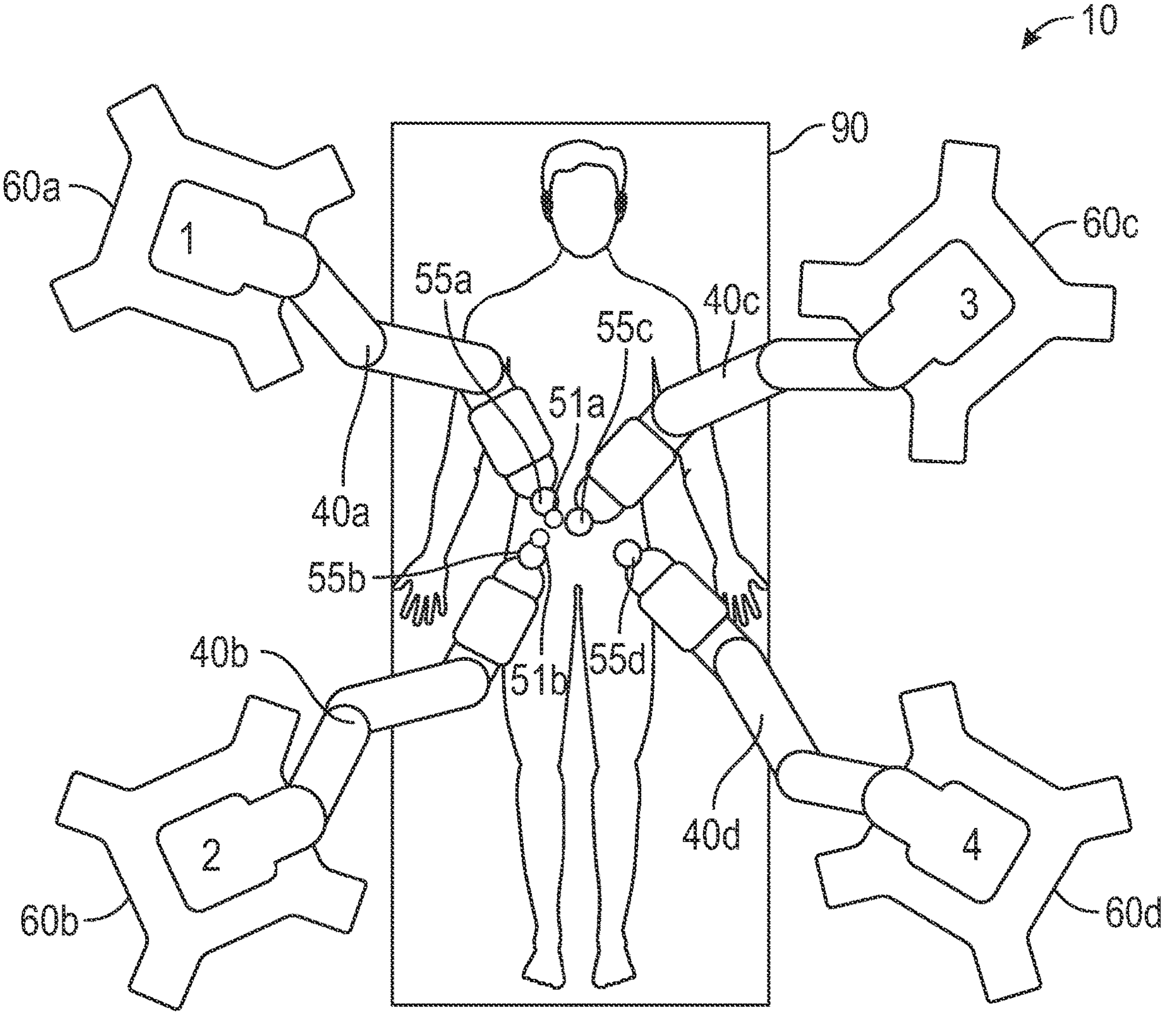
FIG. 5 is a plan schematic view of movable carts of FIG. 1 positioned about a surgical table according to an aspect of the present disclosure.

With reference to FIG. 5, the surgical robotic system 10 is setup around a surgical table 90. The system 10 includes movable carts 60*a-d*, which may be numbered "1" through "4." During setup, each of the carts 60*a-d* are positioned around the surgical table 90. Position and orientation of the carts 60*a-d* depends on a plurality of factors, such as placement of a plurality of access ports 55*a-d*, which in turn, depends on the surgery being performed. Once the port placements are determined, the access ports 55*a-d* are inserted into the patient, and carts 60*a-d* are positioned to insert instruments 50 and a plurality of endoscopic cameras 51*a* and 51*b*.

The system 10 may include a plurality of cameras, e.g., cameras 51*a* and 51*b*. The cameras 51*a* and 51*b* may be coupled to and controlled by their respective robotic arms 40. The cameras 51*a* and 51*b* may be configured for open and/or endoscopic imaging, i.e., coupled to an endoscope, which may be flexible or rigid. The cameras 51*a* and 51*b* may be mono or stereoscopic, i.e., configured to capture two side-by-side (left and right) images of the surgical site to produce a video stream of the surgical scene. In further embodiments, the cameras 51*a* and 51*b* may be mounted to any suitable arm, holder, or held by a user.

The cameras 51*a* and 51*b* are coupled to a video processing device 56 (FIG. 1), which may be disposed within the control tower 20. The video processing device 56 may be any computing device as described below configured to receive the video feed from the cameras 51*a* and 51*b* and output the processed video stream. The video processing device 56 is connected to the cameras 51*a* and 51*b* through a frame grabber, which is configured to capture individual, digital still frames from a digital video stream. The frame grabber is coupled via peripheral component interconnect express (PCI-E) bus to a first processing unit and a second processing unit. The first processing unit may be configured to perform operations, calculations, and/or set of instructions described in the disclosure and may be a hardware processor, a field programmable gate array (FPGA), a digital signal processor (DSP), a central processing unit (CPU), a microprocessor, and combinations thereof. Those skilled in the art will appreciate that the processor may be any logic processor (e.g., control circuit) adapted to execute algorithms, calculations, and/or set of instructions described herein. The second processing unit may be a graphics processing unit (GPU) or an FPGA, which is capable of more parallel executions than a CPU (e.g., first processing unit) due to a larger number of cores, e.g., thousands of compute unified device architecture (CUDA) cores, making it more suitable for processing images.

The video processing device also includes various other computer components, such as RAM, a storage drive, peripheral ports, input device (e.g., touch screen). Additionally, the video processing device is also coupled to one or more displays via output ports. The video processing device is configured to output the processed images through any suitable video output port, such as a DISPLAYPORT™, HDMI®, etc., that is capable of transmitting processed images at any desired resolution, display rates, and/or bandwidth.

Figure 6:
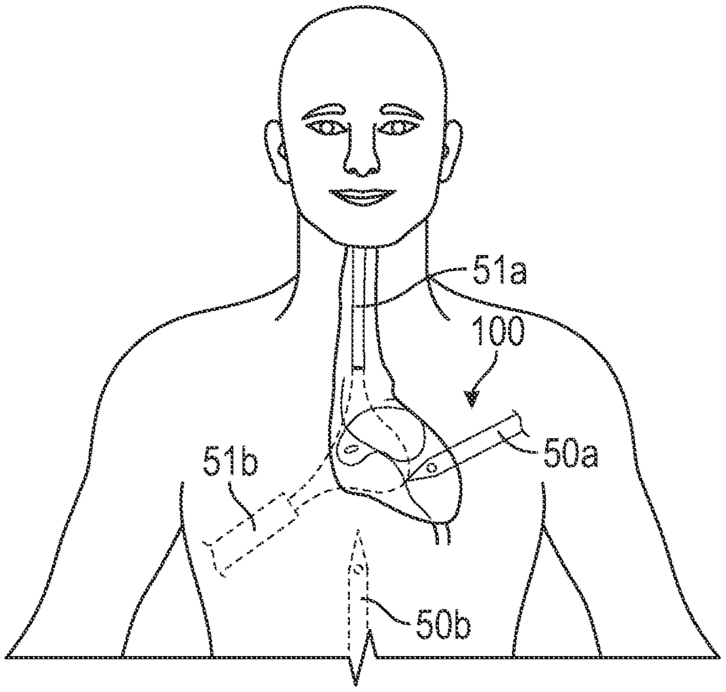
FIG. 6 is a side cross-sectional view of a patient with an imaging system having multiple cameras according to an embodiment of the present disclosure.
Figure 7:
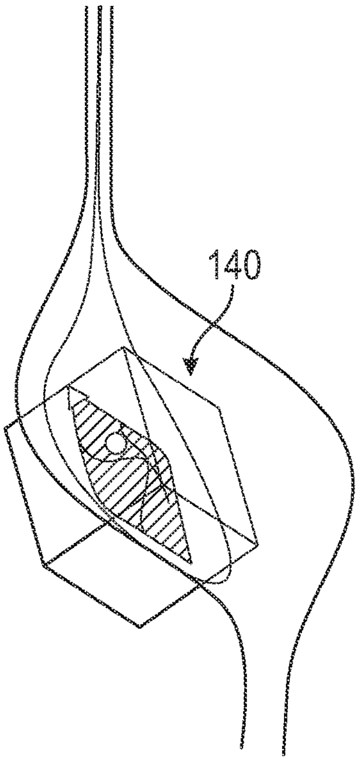
FIG. 7 is a 3D volume including modified video streams of an organ imaged using the imaging system of FIG. 6.

With reference to FIG. 6, a multiple camera imaging system 100 includes the cameras 51*a* and 51*b*, which provide different views of the patient and/or surgical site where the fields of view (FOV) are separated by an obstruction, such as tissue (i.e., organ, abdominal wall, lumen wall, etc.) thereby imaging opposing tissue surfaces. In an illustrative embodiment, the second camera 51*b* is inserted into an abdominal cavity, with an organ "O" (e.g., stomach) being within the FOV of the second camera 51*b* to provide an external view of the organ "O" or the surgical site. The first camera 51*a* is inserted into the organ "O" to provide an internal view of the organ "O" or the surgical site. Multiple instruments 50*a* and 50*b* may be used as shown in FIG. 6.

As shown in FIG. 6, the imaging system 100 may be used in bariatric procedures. The second camera 51*b* may be flexible and may be inserted transorally or transnasally and may be used to identify and localized restrictions of the pathway, e.g., esophagus. The first camera 51*a* may be inserted into the abdominal cavity through the access port 55*b*.

The imaging system 100 may also be used in colorectal surgical procedures, such as anastomosis, with the second camera 51*b* being inserted transanally to provide the view of the anastomosis site while the first camera 51*a* is inside the abdominal cavity providing the exterior view of the colon or the anastomosis site. The imaging system 100 may also be used in localizing tumors in the colon or rectum by positioning cameras 51*a* and 51*b* inside and outside the colon and/or large intestine, respectively.

In urological procedures, the second camera 51*b* may be inserted through the urethra while the first camera 51*a* is inserted into the abdomen. In gynecological procedures (e.g., hysterectomy), the second camera 51*b* may be inserted transvaginally and the first camera 51*a* may be inserted into the abdominal cavity through the access port 55*b*.

The imaging system 100 may also be used in thoracic cavity procedures, such as lung surgeries. The second camera 51*b* may be coupled to a bronchoscope and may be inserted transorally or transnasally, whereas the first camera 51*a* may be inserted through the abdominal wall as described above.

The imaging system 100 may also be used during abdominal surgeries to establish pneumoperitoneum and to insert cameras to establish visualization of the abdominal cavity. During these phases, the second camera 51*b* may be disposed outside of the patient while the first camera 51*a* is being inserted into the abdominal cavity. This configuration allows the second camera 51*b* to monitor the position and insertion of the first camera 51*a*.

The image processing device 56 is configured to receive multiple video streams from the cameras 51*a* and 51*b* and to combine and/or augment the video streams to generate one or more 3D volumes as shown in FIGS. 7-11 including modified video streams that are displayed on the surgeon console 30 (e.g., the first screen 32 and/or the second screen 34). The image processing device 56 may be also configured to output a first video stream from the second camera 51*b* on the first screen 32 and a second video stream from the first camera 51*a* on the second screen 34. Each of the first and second video streams may be also augmented with the counterpart video stream. The user may select which of the video streams is shown on which of the screens 32 and 34. The imaging system 100 may include a GUI providing users with buttons and other inputs or menus to control the first and second video streams, including switching the streams between the screens 32 and 34 and other features of the present disclosure described herein.

In embodiments, the user may also switch between which of the first and second cameras 51*a* and 51*b* is being used in hand-eye coordination in controlling the surgeon console 30. In particular, the surgeon console 30 is configured to track eye gaze of the user and to coordinate surgeon's gaze with user engagement with the hand controllers 38*a* and 38*b*. Thus, the hand-eye coordination depends on which camera is being controlled. The GUI of the screens 32 and 34 may be used to select which of the first and second cameras 51*a* and 51*b* is the main camera that is used for hand-eye coordination.

The first and second video streams may be combined in a variety of ways. The first video stream from the second camera 51*b* may be the main view shown on the first screen 32 of the surgeon console 30 with the second video stream being shown in a picture-in-picture (PIP) on the first screen 32 or on the second screen 34. In embodiments, the PIP view may be located and/or sized automatically by the surgeon console 30 based on the position of the first camera 51*a* or based on surgical action, phase, or step of the surgical procedure.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 50 (e.g., forceps) are used to achieve a specific objective by performing one or more surgical actions.

In some examples, the system 10 may include a machine learning processing system having a phase detector that uses the machine learning models to identify the surgical action, phase, or step within the surgical procedure ("procedure"). Phase detector uses a particular procedural tracking data structure from a list of procedural tracking data structures. Phase detector selects the procedural tracking data structure based on the type of surgical procedure that is being performed. In one or more examples, the type of surgical procedure is predetermined or input by the user. The procedural tracking data structure identifies a set of potential phases that can correspond to a part of the specific type of procedure. In further embodiments, the phase detector may detect the surgical action, phase, or step by image processing the first and/or second video streams.

The first video stream, which includes the internal view may also be augmented by the second video stream, which includes the external view. The first video stream may be augmented to provide a transparent or a partially transparent view of the organ "O". In particular, the first and second video streams may be used to generate a 3D volume having a first augmented video stream, in which a portion of the exterior image of the organ "O" (i.e., of the first video stream) is removed and replaced with a reconstructed portion based on the interior image of the organ "O" (i.e., of the second video stream). Reconstruction of the image may be performed using machine learning image processing algorithms that generate textures and depth maps of the imaged objects. In particular, the video processing device 56 is configured to generate depth maps of tissue surfaces in the first and second video streams. A second augmented stream may be also generated by replacing a portion of the interior image of the organ "O" (i.e., of the second video stream) with a reconstructed portion based on the exterior image of the organ "O" (i.e., of the first video stream). The 3D volume with the first augmented video stream may be shown on the first screen 32 and the second augmented video stream may be shown on the second screen 34, providing the user with multiple augmented views by removing obstructions between the first and second FOVs of the first and second cameras 51*a* and 51*b*.

With reference to FIGS. 7-10 various views of a 3D volume 140 generated from the first and second video streams are shown. The video streams may be used to generate the 3D volume 140, e.g., a cube, that may be manipulated (e.g., zoom, pan, rotate) to provide any suitable view to the user on one the screens 32, 34, etc. The 3D volume 140 may be a hybrid view including real-time augmented video stream and virtual, computer-generated objects and images. The first and second videos may be processed to generate depth maps and are used to overlay virtual markers, such as a dot, a shape, etc.

Figure 8:
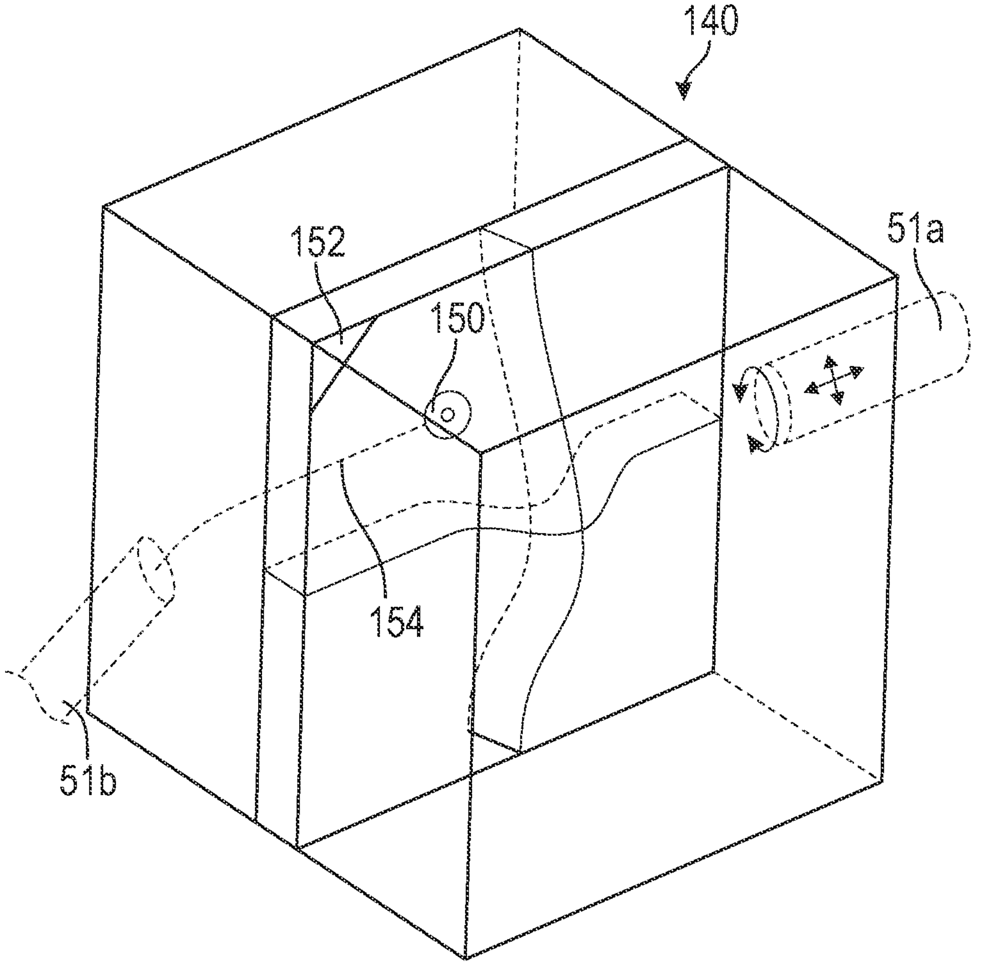
FIG. 8 is an enlarged view of the 3D volume of FIG. 7.
Figure 9:
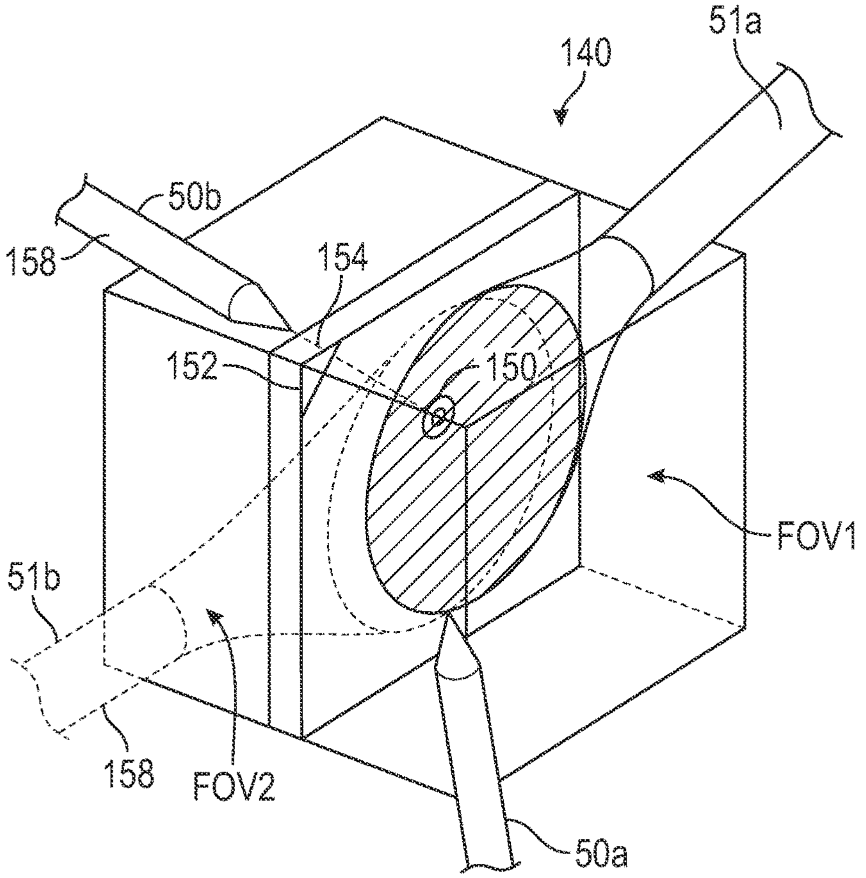
FIG. 9 is an augmented view of the 3D volume of FIG. 7.
Figure 10:
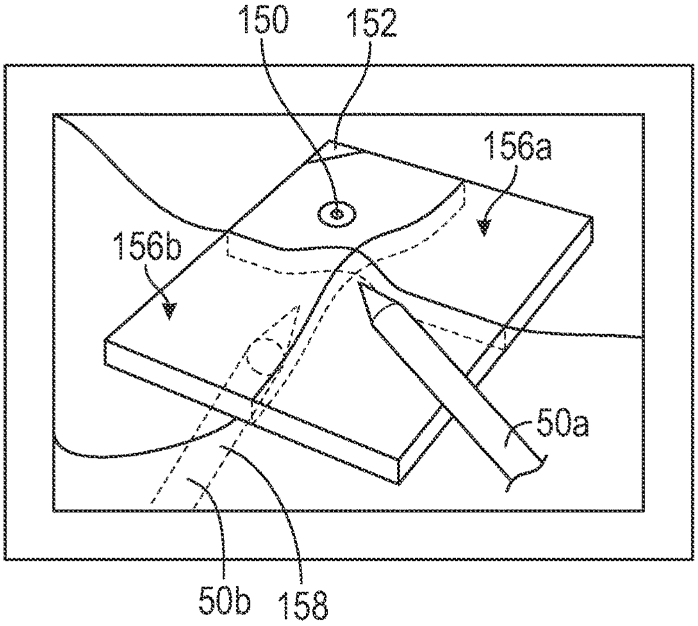
FIG. 10 is a stitched view of the 3D volume of FIG. 7.

As shown in FIGS. 8 and 9, a virtual marker 150 may be placed based on a trajectory 154 (i.e., central optical axis) of the device, e.g., cameras 51*a* and 51*b* and/or instruments 50*a* and 50*b*. In further embodiments, the trajectory 154 of insertion or movement of the device may be overlayed on the 3D volume 140 to allow for planning of movement of the device through tissue where the field of view of the cameras 51*a* or 51*b* is blocked. The virtual marker 150 moves as the devices are moved, this allows for tracking of the devices even when they are obscured by tissue. In addition to the virtual marker 150, an orientation marker 152 may also be displayed to aid in orientation and may be placed in a corner of the view. In embodiments, additional virtual markers may be displayed, which may be a line or a boundary to demarcate tissue being resected or otherwise operated on.

With continued reference to FIGS. 8 and 9, the 3D view may be also processed to only show a desired portion of the tissue, e.g., inside of the organ "O", and to eliminate other surrounding tissue from the augmented video stream. Thus, only a portion of the tissue that blocks the fields of view FOV1 and FOV2 of the cameras 51*a* and 51*b*, respectively, between the two cameras 51*a* and 51*b* is maintained. In further embodiments, 3D view may also include virtual representations 158, e.g., shaded, dotted lines, etc., of the devices that are obscured, e.g., second camera 51*b*, second instrument 50*b*.

As shown in FIG. 9, the 3D volume may be manipulated by the user or the system 10 to provide any suitable point of view, thus rotation or otherwise changing the view of the 3D volume 140 results in rendering obscured devices as virtual objects and vice versa, previously obscured objects are shown in real time as they are imaged by the cameras 51*a* and 51*b*. The virtual marker 150 and the orientation marker 152 are also displayed and are moved to track the devices with which the virtual marks 150 are associated with.

Additional modifications and enhancements of the video streams may include providing an overhead (e.g., 2D) or 3D schematic map with cameras 51*a* and 51*b* and their corresponding FOVs as well showing orientation indicators in each video stream. A 2D or 3D schematic map may be displayed on any of the screens 32 or 34 and allows the user to see positioning of the instrument 50, the first and second cameras 51*a* and 51*b* relative to each other since these objects are not viewable by an outside camera.

Figure 11:
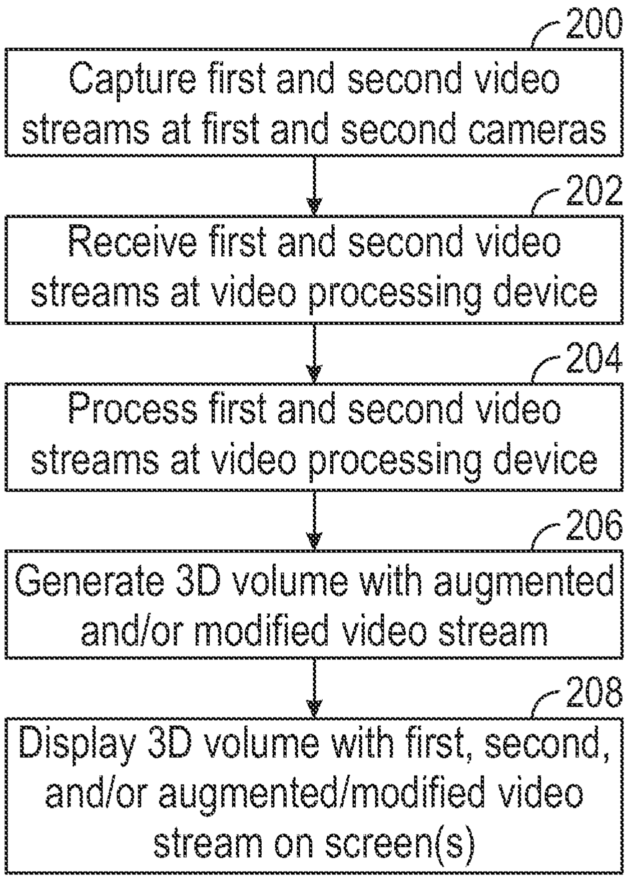
FIG. 11 is a flow chart of a method of receiving video data from multiple cameras according to an embodiment of the present disclosure.

The cameras 51*a* and 51*b* may also be used to image the same continuous object, e.g., abdominal cavity. With reference to FIG. 11, the video streams or portions 156*a* and 156*b* (e.g., FOVs of cameras 51*a* and 51*b*) may be stitched together to enable simultaneous localization and mapping to build an anatomical map of the tissue regions being imaged as the cameras 51*a* and 51*b* are moved. The boundary between the two video streams may be manipulated (e.g., stretched, bent, made at least partially transparent, etc.) to allow for the cameras 51*a* and 51*b* to view each other orthogonally. In particular, the video processing device 56 is configured to make one or more of the following corrections, 1) eliminate image distortion resulting from various optical aberrations for accurate overlapping of images from the camera, 2) compensate for exposure, to match the lighting conditions on the images of all cameras, 3) connect object lines to ensure seamless transition between images so they do not appear broken or discontinuous, and correct image occlusion to prevent overlapping and/or doubling of objects captured by the cameras 51*a* and 51*b*. The orientation of the stitched images made be adjusted for the convenience or ease of use of the clinician. In some embodiments, the modified video stream may be automatically rotated or selectively rotated by the clinician. In some embodiments, the system automatically switches between a first stream, second stream, and modified video stream based on machine learning processes that identify phases, tasks, events, or other surgical events. In other embodiments, a menu is provided to the clinician.

Multiple video streams may also be used to detect critical structures, such as cystic duct, arteries, etc. using machine learning image processing techniques. In particular, different FOVs of the same object may be used to compare two images of the same object to provide for more accurate identification of the critical structures than a single camera view. Once identified, the critical structures may be highlighted on the first and/or second video streams to allow the surgeon to avoid accidentally injuring the structures during operation on neighboring tissue. Highlighting may be done by coloring the structures and/or drawings a boundary. In further embodiments, the critical structures may be labeled.

In further embodiments, at least one of the second camera 51*b* or the first camera 51*a* may be an infrared camera configured to capture near infrared (NIR) or infrared light that is used to illuminate tissue. The NIR images may be used to highlight specific tissue regions in the combined video stream or in the stream of the camera providing NIR images.

With reference to FIG. 11 a method of using two cameras 51*a* and 51*b* includes capturing first and second video streams of opposing tissue surfaces at step 200. This may include placing the second camera 51*b* outside the organ "O" and the first camera 51*a* inside the organ "O", as described above. At step 202, the video processing device 56 receives the video streams and processes them at step 204. The video processing device 56 generates the 3D volume 140 including augmented or modified video streams in a manner described above (e.g., filling in video streams with portions from counter streams, including virtual markers, etc.) at step 206. The first, second, and modified video streams are then displayed at step 208 on the screens 32, 34 of the surgeon console 30 allowing the surgeon to modify the views.

While the present disclosure was described with using two cameras, the system and method according to the present disclosure may be implemented using three or more cameras. In particular, a plurality of video streams may be used to generate one, two, or more combined video streams and/or some or all of the video streams may be augmented with video streams of counterpart cameras.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An imaging system comprising:

a first camera configured to capture a first video stream of a first tissue surface;

a second camera configured to capture a second video stream of a second tissue surface, wherein the first tissue surface includes an internal surface of a tissue structure and the second tissue surface includes an external surface of the tissue structure, such that the first and second tissue surfaces are opposing surfaces of a common tissue wall, wherein the first camera is inserted into the tissue structure to capture the first video stream of the internal surface and the second camera is positioned outside the tissue structure to capture the second video stream of the external surface;

a video processing device configured to:

receive the first video stream from the first camera and the second video stream from the second camera; and modify at least one the first video stream or the second video stream based on one of the first video stream or the second video stream to generate a 3D volume having a modified video stream, wherein the modified video stream includes an augmented view of the tissue structure generated by replacing a portion of one of the first video stream or the second video stream depicting the common tissue wall with a reconstructed portion based on the other of the first video stream or the second video stream capturing the opposing surface of the common tissue wall; and a first screen coupled to the video processing device and configured to display the 3D volume having the modified video stream.

2. The imaging system according to claim 1, further comprising:

a second screen coupled to the video processing device.

3. The imaging system according to claim 2, wherein the video processing device is configured to output at least one of the first video stream, the second video stream, or 3D volume having the modified video stream on at least one of the first screen or the second screen.

4. The imaging system according to claim 1, wherein in modifying the first video stream, the video processing device is further configured to remove a portion of the first video stream.

5. The imaging system according to claim 4, wherein in modifying the first video stream, the video processing device is further configured to fill in the portion of the first video stream with a reconstructed portion of the second video stream.

6. The imaging system according to claim 5, wherein the video processing device is further configured to generate a depth map of the first and second tissue surfaces and generate the reconstructed portion based on the depth map.

7. The imaging system according to claim 2, wherein the video processing device is further configured to generate a virtual marker in the 3D volume having the modified video stream.

8. The imaging system according to claim 2, wherein at least one of the first screen or the second screen includes a graphical user interface configured to select at least one of the first screen or the second screen to display at least one of the first video stream, the second video stream, or the 3D volume having the modified video stream.

9. A surgical robotic system comprising:

a first robotic arm including a first camera located at a first position and configured to capture a first video stream of a first tissue surface;

a second robotic arm including a second camera located at a second position and configured to capture a second video stream of a second tissue surface, wherein the first tissue surface includes an internal surface of a tissue structure and the second tissue surface includes an external surface of the tissue structure, such that the first and second tissue surfaces are opposing surfaces of a common tissue wall, wherein the first camera is inserted into the tissue structure to capture the first video stream of the internal surface and the second camera is positioned outside the tissue structure to capture the second video stream of the external surface;

a third robotic arm including a surgical instrument;

a video processing device configured to:

receive the first video stream from the first camera and the second video stream from the second camera;

combine the first video stream based on the second video stream to generate a combined video stream based on the first position and the second position; and generate a 3D volume including a trajectory of at least one of the first camera, the second camera, or the instrument based on the combined video stream, wherein the combined video stream includes an augmented view of the tissue structure generated by replacing a portion of one of the first video stream or the second video stream depicting the common tissue wall with a reconstructed portion based on the other of the first video stream or the second video stream capturing the opposing surface of the common tissue wall; and a surgeon console including a first screen coupled to the video processing device and configured to display the combined video stream.

10. The surgical robotic system according to claim 9, wherein the surgeon console further includes a second screen coupled to the video processing device.

11. The surgical robotic system according to claim 10, wherein the video processing device is configured to output at least one of the first video stream, the second video stream, or the combined video stream on at least one of the first screen or the second screen.

12. The surgical robotic system according to claim 9, wherein in combining the first video stream, the video processing device is further configured to stitch the first video stream with the second video stream.

13. The surgical robotic system according to claim 12, wherein in combining the first video stream, the video processing device is further configured to fill in a portion of the first video stream with a reconstructed portion of the second video stream.

14. The surgical robotic system according to claim 13, wherein the video processing device is further configured to generate a depth map of the first and second tissue surfaces and generate the reconstructed portion based on the depth map.

15. The surgical robotic system according to claim 9, wherein the video processing device is further configured to generate a virtual marker in the combining video stream.

16. The surgical robotic system according to claim 15, wherein the virtual marker is placed at a location within a field of view of the second camera.

17. A method of imaging tissue, comprising:

capturing a first video stream of a first tissue surface at a first camera;

capturing a second video stream of a second tissue surface at a second camera, wherein the first tissue surface includes an internal surface of a tissue structure and the second tissue surface includes an external surface of the tissue structure, such that the first and second tissue surfaces are opposing surfaces of a common tissue wall, wherein the first camera is inserted into the tissue structure to capture the first video stream of the internal surface and the second camera is positioned outside the tissue structure to capture the second video stream of the external surface;

receiving the first video stream from the first camera at a video processing device;

receiving the second video stream from the second camera at the video processing device;

modifying the first video stream based on the second video stream to generate a 3D volume having a modified video stream, wherein the modified video stream includes an augmented view of the tissue structure generated by replacing a portion of one of the first video stream or the second video stream depicting the common tissue wall with a reconstructed portion based on the other of the first video stream or the second video stream capturing the opposing surface of the common tissue wall; and displaying the 3D volume having the modified video stream on a screen coupled to the video processing device.

18. The method according to claim 17, wherein modifying the first video stream at the video processing device further includes removing a portion of the first video stream.

19. The method according to claim 18, wherein modifying the first video stream at the video processing device further includes filling in the portion of the first video stream with a reconstructed portion of the second video stream.

20. The method according to claim 19, wherein in modifying the first video stream at the video processing device further includes generating a depth map of the first and second tissue surfaces and generating the reconstructed portion based on the depth map.

* * * * *